United States Patent [19]
Munoz et al.

[11] Patent Number: 5,383,844
[45] Date of Patent: Jan. 24, 1995

[54] HUMERAL FRACTURE BRACE

[75] Inventors: Eugene J. Munoz, Redding; Miguel Estupinan, Oceanside; Charles A. Bastyr, San Diego, all of Calif.

[73] Assignee: Smith & Nephew Donjoy, Inc., Carlsbad, Calif.

[21] Appl. No.: 948,123

[22] Filed: Sep. 21, 1992

[51] Int. Cl.6 .............................. A61F 5/04; A61F 5/10
[52] U.S. Cl. ........................................ 602/20; 602/5; 606/54; 606/57
[58] Field of Search .................... 602/4, 5, 12, 16, 20, 602/21, 23, 26, 27; 606/53, 54, 57

[56] References Cited

U.S. PATENT DOCUMENTS

| | | | |
|---|---|---|---|
| 1,466,487 | 8/1923 | Shaffer | 602/16 |
| 2,310,566 | 2/1943 | Anderson | 602/20 |
| 2,332,440 | 3/1953 | Hauser et al. | 602/23 X |
| 2,339,515 | 1/1944 | Parcher | 602/19 |
| 3,028,858 | 4/1962 | Cutler | 602/20 |
| 3,826,251 | 7/1974 | Ross | 602/16 |
| 4,180,870 | 1/1980 | Radulovic et al. | 602/20 X |
| 4,433,679 | 2/1984 | Mauldin et al. | 602/20 X |
| 4,436,088 | 3/1984 | Finnieston | 602/20 |
| 4,489,718 | 12/1984 | Martin | 602/26 X |
| 4,494,534 | 1/1985 | Hutson | 602/16 |
| 4,559,932 | 12/1985 | Salort | 602/20 |
| 4,572,172 | 2/1986 | Williams | 602/4 |
| 4,576,153 | 3/1986 | Zagorski et al. | 602/25 |
| 4,598,702 | 7/1986 | Lilla | 602/4 |
| 4,598,703 | 7/1986 | Lindemann | 602/4 |
| 4,896,660 | 1/1990 | Scott | 602/4 |
| 5,009,223 | 4/1991 | DeFonce | 602/16 |
| 5,013,037 | 5/1991 | Stermer | 602/16 X |
| 5,033,461 | 7/1991 | Young et al. | 602/20 X |
| 5,074,291 | 12/1991 | Carter | 602/21 X |
| 5,156,168 | 10/1992 | Canterna | 602/21 X |
| 5,171,310 | 12/1992 | Chisena | 602/20 X |
| 5,203,763 | 4/1993 | Lajiness-O'Neill | 602/20 X |

FOREIGN PATENT DOCUMENTS

| | | | |
|---|---|---|---|
| 1280471 | 10/1968 | Germany | 602/20 |
| 1150072 | 4/1969 | United Kingdom | 602/20 |
| 321252 | 11/1971 | U.S.S.R. | 602/4 |
| WO91/06265 | 5/1991 | WIPO | |

Primary Examiner—Robert A. Hafer
Assistant Examiner—Brian E. Hanlon
Attorney, Agent, or Firm—Pravel, Hewitt, Kimball & Krieger

[57] ABSTRACT

A humeral fracture brace for providing rigid lateral support to the humerus which includes a humeral cuff that is pivotally connected to a forearm support by a sliding hinge that allows the forearm support to slide relative to the axis of the humeral cuff. The forearm support includes a rigid brace bar and a generally U-shaped cuff for engaging a patient's wrist. An adjustable shoulder strap with a slidable pad is connected between the humeral cuff and the forearm support.

7 Claims, 2 Drawing Sheets

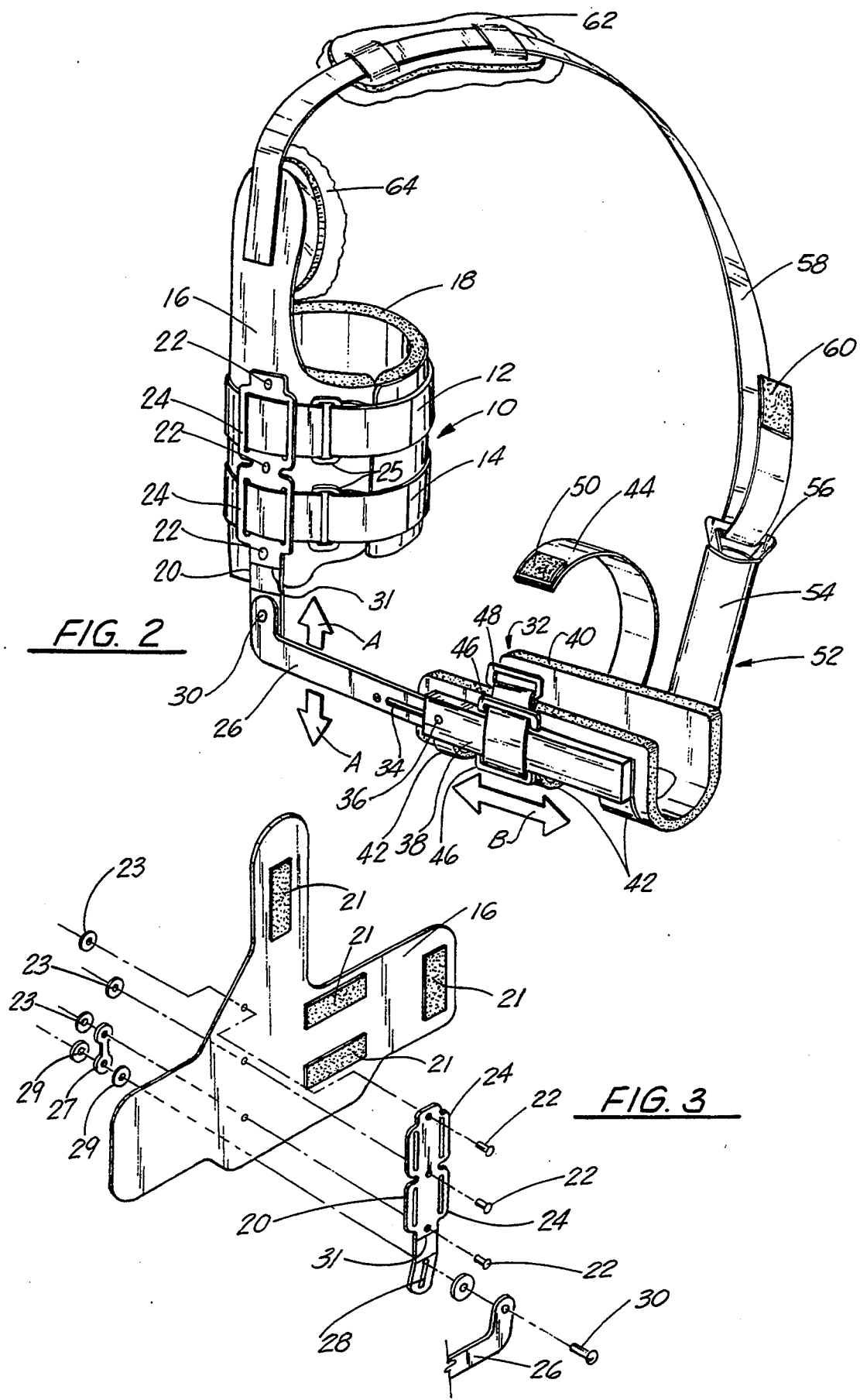

HUMERAL FRACTURE BRACE

FIELD OF THE INVENTION

The present invention relates to orthotic devices, and more particularly, to a fracture brace for the post trauma treatment of fractures of the humeral shaft.

BACKGROUND OF THE INVENTION

Numerous braces are known which are useful for maintaining broken bone segments of the upper arm or humerus in a fixed position during healing. The most common type of brace is a plaster cast which has the disadvantage of being heavy, uncomfortable and cumbersome. Various braces of semi-rigid material have been used for external fixation of upper arm fractures. Braces of this type are shown and described in U.S. Pat. Nos. 4,436,088 and 4,576,153, where a bracing member supports the humerus without stabilizing the remaining portions of the patient's arm.

U.S. Pat. No. 1,466,487 is directed to a more supportive humeral brace that is clamped to the shoulder and pivotally connected to a forearm support. However, the brace provides no support to the patient's wrist, nor does it allow for anything but pivotal movement between the humeral and forearm support.

SUMMARY OF THE INVENTION

The invention is directed to a brace for supporting a fractured humerus, which has both a humeral support and a forearm support. The humeral support is formed of a circumferential cuff which has a pair of tensioning straps for allowing differential compressive connections to the humerus.

The humeral support has a plastic shell and rigid brace bar for holding the fractured portions of the humerus in place relative to each other, the brace bar being connected to a forearm brace bar through a sliding hinge and resilient or elastic member which urges the brace bar toward the humerus. Appropriate pads are provided between the plastic shell and humerus. The hinge allows for relative pivotal movement between the forearm brace bar and the humeral brace bar and at the same time permits the forearm brace bar to move along the axis of the humeral brace bar so that traction/distraction of the fracture can be accomplished through weights added to the forearm of the patient.

The forearm brace bar includes a longitudinal bar and a cuff that supports the wrist and hand of the patient for controlling the forearm angle relative to the humeral bar and to allow immobilization of the forearm. The wrist/hand cuff can be slidably connected to the forearm brace bar to accommodate different forearm lengths. The forearm brace can be disconnected from the humeral cuff for greater patient mobility during latter stages of recovery.

A strap is connected between the upper end of the humeral brace and the wrist/hand cuff for immobilizing the forearm at an appropriate angle relative to the humerus. A pad is slidably mounted on the strap for bearing against the neck and shoulder of the patient to better distribute weight from the strap. A pad is also mounted on the inner surface of the upper portion of the humeral brace, which bears against the patient's deltoid muscle in order to distribute weight at that location. Weight is thus distributed in three places, at the wrist/hand cuff, the pad mounted on the strap and the deltoid pad.

BRIEF DESCRIPTION OF THE DRAWINGS

In order to acquire a better understanding of the invention, reference may be had to the detailed description of exemplary embodiments, set forth below, considered in conjunction with the appended drawings, in which:

FIG. 2 is a perspective view of the fracture brace of the present invention;

FIG. 3 is an exploded perspective view of the connections between components of the humeral cuff and between the humeral cuff and the forearm brace bar.

DETAILED DESCRIPTION OF AN EXEMPLARY EMBODIMENT

Figure 1:
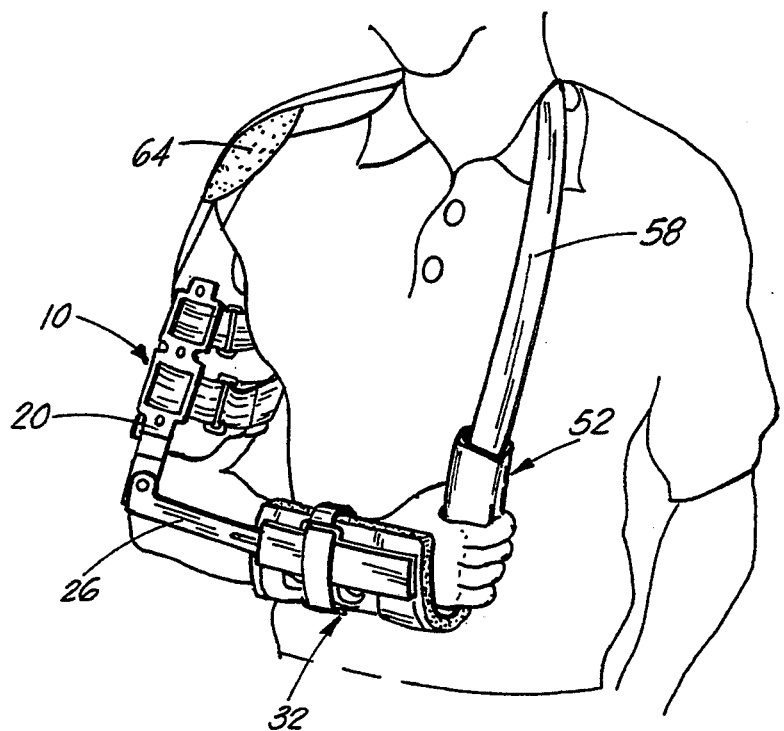
FIG. 1 is a schematic view of the humeral fracture brace applied to a patient.

Referring to the drawings, the brace of the present invention is shown, with FIG. 1 showing in particular how it is worn by a patient. The brace has a humeral cuff 10 which is connected to the humerus of the patient through a pair of tensioning straps 12, 14 so that the compression on the humerus can be controlled.

The humeral cuff 10 is formed of a plastic shell 16 which engages the humerus through a padded liner 18 formed of an open cell foam material. A rigid brace bar 20 is connected to the outer surface of the shell 16 through rivets or screws 22. The plastic shell is rigid enough to provide support to hold broken bone fragments in the humerus together, but flexible enough to open sufficiently for placement around the humerus as shown in FIG. 1.

The brace bar 20 includes a pair of slotted connection guides 24 through which the tensioning straps 12, 14 are threaded. The straps 12, 14 are formed of a woven fibrous material, with a D-ring 25 connected at one end so the other end can loop through the D-ring 25 and connect to itself through a known hoop and loop connection such as sold under the trademark Velcro ®.

Figure 4:
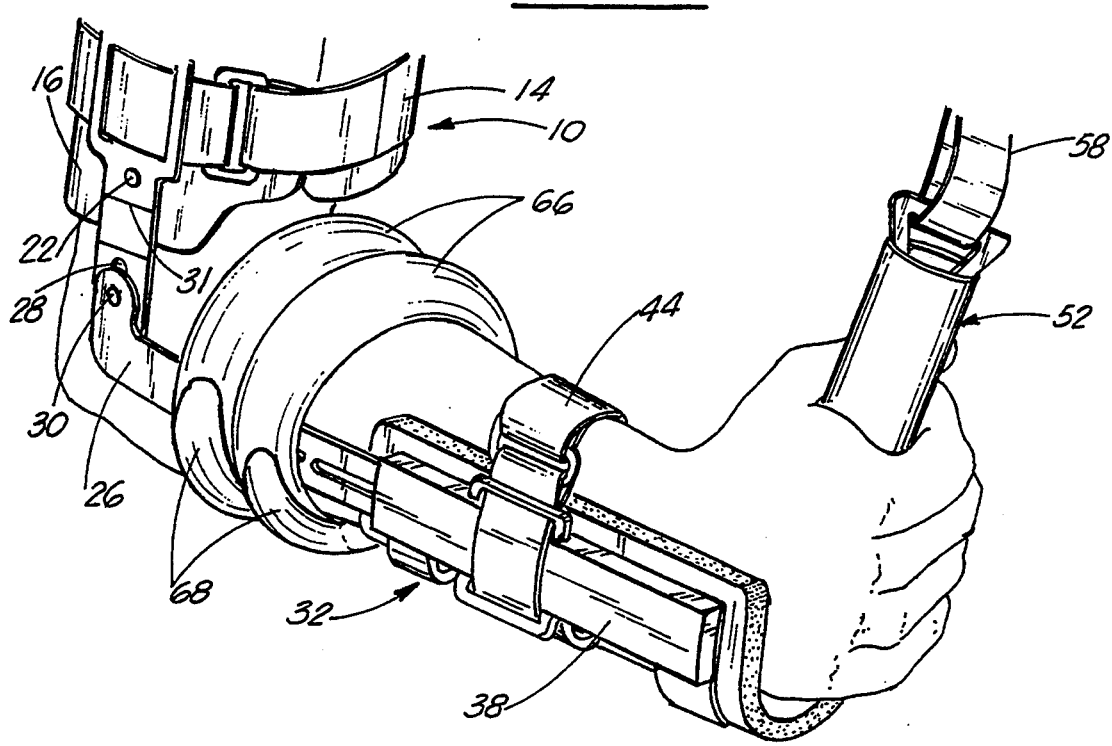
FIG. 4 shows the forearm portion of the fracture brace of FIG. 2 with weights connected to the patient's forearm in order to illustrate the traction/distraction feature.

The brace bar 20 is connected to a forearm brace bar 26 through a sliding hinge which is formed of a slot 28 located at the distal end of humeral brace bar 20 (see FIG. 3), and a pivot pin in the form of a rivet 30, which is mounted on the proximal end of the brace bar 26. The sliding hinge allows the forearm brace bar to move longitudinally relative to the axis of the humeral cuff 10 as shown by the arrows A in FIG. 2, which is advantageous for reasons discussed below when weights are mounted on the patient's forearm as shown in FIG. 4.

FIG. 3 is an exploded perspective view that shows the preferred structure of the humeral cuff 10 and its connection to the brace bar 26. The slotted connection guides 24 are connected to the plastic shell 16 through rivets 22 which are upset after they are passed through washers 23. A spring or elastic element 27 is connected between the rivet 22 closest to the sliding hinge and the rivet 30 for urging the brace bar 26 upwardly toward the humeral cuff 10. The elastic element 27 is formed of any suitable elastomeric material such as a urethane plastic that is strong enough to urge the brace bar 26 upwardly in the slot 28, but resilient enough to allow the brace bar 26 to move downwardly when weights are attached as shown in FIG. 4. Suitable washers 29 are provided between adjacent components. Sections of the hooked gender of hook and loop material 21 such as Velcro® are spaced around the outer surface of the plastic shell to provide a better connection with the straps 12, 14 and the strap 58, described below.

The brace bar 20 is scribed or scored as shown by line 31 so that the portion of the brace bar 20 between the scribe line 31 and the brace bar 26 can easily be broken away from the remaining portion of the humeral cuff 10. This feature allows the brace bar 26 to be disconnected and removed during the final stages of rehabilitation.

A U-shaped cuff 32 for supporting the wrist and hand of the patient is mounted on the distal end of the forearm brace bar 26 through a sliding connection formed of a slot 34 in the forearm brace bar 26 and a pin 36 mounted on a support 38. The cuff 32 is in effect an extension of the forearm brace bar 26 and engages the wrist/hand of the patient through appropriate padding 40 formed of an open cell foam held in place by three U-shaped supports 42.

The sliding connection between the slot 34 and the pin 36 allows the wrist/hand cuff 32 to move back and forth in the direction of arrow B to accommodate different forearm lengths and provide for greater patient comfort. A strap 44, formed of woven fibrous material, extends around the wrist/hand cuff 32 and is threaded through a pair of loops 46 mounted on the extension 38, the strap 44 having a D-loop 48 at one end so that a Velcro® patch 50 of a hooked gender can be passed through the loop 48 and connected to the strap 44.

A hand grip 52 is formed by providing a padded gripping portion 54 over an extension 56 of the outermost U-shaped support 42. The extension 56 is in the form of a loop so that a support strap 58 can be connected between the upper portion of the plastic shell 16 of the humeral cuff 10 and the loop portion 56. The shoulder strap can be adjusted for immobilizing the forearm of the patient at a preselected angle through a Velcro® patch 60 which folds back over a remaining portion of the strap 58. The other end of the strap 58 is connected to the plastic shell 16 through a hook and loop connection formed between the hooked section 21 shown in FIG. 3 and the woven fibrous material of the strap 58 so that the strap can be removed when it is no longer needed by the patient.

A shoulder/neck pad 62 is slidably connected to the strap 58 for distributing loads to the shoulder and neck of the patient. A deltoid pad 64 is mounted on the inner surface of the plastic shell 16 for distributing loads to the shoulder of the patient at the location of the deltoid muscle, as best shown in FIG. 1.

When the humeral brace as described is used on a patient, the humeral fracture is stabilized through what is called 3-point stabilization. This means that while the fractured bone sections are immobilized, optimum control and comfort at the fracture site are provided through primary contact at the wrist/hand cuff 32, the neck/shoulder pad 62, and the deltoid pad 64. This system provides for more even distribution of weight while the patient is wearing the brace, while at the same time reducing stresses at the fracture site.

By providing the sliding hinge between the humeral brace bar 20 and the forearm brace bar 26, traction/distraction on the fracture can be accomplished without altering the position of the humeral cuff 10, through the addition of one or more weights 66 on the forearm of the patient as shown in FIG. 3. These weights 66 can be generally U-shaped with a strap 68 for connecting the ends together after they are in the position shown in FIG. 4. When the weights 66 are attached, the brace bar 26 will move away from the humeral cuff 10, overcoming resistance of the material which forms the elastic member 27 (see FIG. 3).

The humeral brace described above has been found to be an extremely versatile alternative to casting and can be used for support and containment immediately after reduction of the fracture throughout the entire recovery period and during the final stages of rehabilitation. The rigid connection between the humeral cuff 10 and the patient's arm allows the fracture to heal properly. The vertical sliding hinge allows the fractured portions to be placed in traction/distraction during the initial stages of recovery without having to change the position of the humeral cuff 10. By separating brace bar 20 at the scribe line 31, the distal end of the brace bar 20 and brace bar 26 may be removed during the final stages of rehabilitation to provide the patient with greater mobility.

The design provides for a rigid, yet lightweight brace that is extremely comfortable to wear because of the three-point stabilization system. The patient is allowed maximum mobility without sacrificing the need to maintain the fractured bone totally immobile during the earlier stages of recovery. While the brace is worn, joint motion at the shoulder, elbow, wrist and fingers is possible without sacrificing stability at the fracture site. This allows exercises to be started at an early time during the recovery period, which significantly reduces muscle atrophy and shortens rehabilitation time.

It should be understood that the foregoing description is exemplary of the invention and not restrictive, and that improvements and modifications can be made to the invention without departing from the spirit and scope of the invention as defined in the appended claims.

We claim:

1. Humeral fracture brace, comprising:
   a) a humeral cuff for providing rigid lateral support to the humerus;
   b) a humeral brace bar extending from the humeral cuff along a line that tracks the patient's humerus, the bar having a proximal end portion that joins to the cuff and a distal end portion;
   c) a forearm support that includes a forearm cuff and a forearm brace bar extending from the forearm cuff along a line that tracks the patient's forearm, the forearm brace bar having a proximal end portion that is joined to the distal end portion of the humeral brace bar and a distal end portion that joins to the forearm cuff;
   d) sliding hinge means for joining the distal end of the humeral brace bar and the proximal end of the forearm brace bar, said hinge means including a longitudinal slot in the distal end portion of the humeral support bar and a pivot pin in the proximal end of the forearm brace bar, said sliding hinge means allowing the proximal end portion of the forearm brace bar to slide relative to the axis of the humeral brace bar;
   e) a sliding connection that connects the forearm cuff to the forearm support bar;
   f) spring means for urging the proximal end of the forearm support bar toward the humeral cuff, said spring means connected at a first end to said humeral brace bar distal end portion and connected at a second end to said pivot pin; and g) weight means adapted to encircle the patient's forearm for translating the pivot pin in the slot to offset the spring means, allowing traction/distraction of the fracture.

2. The brace of claim 1, wherein the humeral cuff includes a plastic shell and a padded liner for the shell.

3. The brace of claim 2 and further including a pair of tensionable straps for connecting the humeral cuff to a patient's upper arm.

4. The brace of claim 1, wherein the spring means includes a resilient member.

5. The brace of claim 1, and further including an adjustable shoulder strap for connection between the humeral cuff and the forearm support.

6. The brace of claim 5 wherein the shoulder strap includes a pad slidably connected to the strap for distributing weight to the patient's shoulder.

7. The brace of claim 5, and further including a deltoid pad connected to the inner surface of the humeral cuff adjacent to the patient's deltoid for distribution of weight to the patient's deltoid.

* * * * *